United States Patent [19]
Sasaki et al.

[11] Patent Number: 5,747,310
[45] Date of Patent: May 5, 1998

[54] **GENE INTEGRATION INTO CHROMOSOMES OF *LACTOBACILLUS DELBRUECKII* SPECIES AND INTEGRANTS THEREOF**

[75] Inventors: Takashi Sasaki; Yasuko Sasaki; Yoshiyuki Ito; Kumi Otsu, all of Odawara, Japan

[73] Assignee: Meiji Milk Products Co., Ltd., Tokyo, Japan

[21] Appl. No.: 760,335

[22] Filed: Dec. 4, 1996

Related U.S. Application Data

[63] Continuation of Ser. No. 193,055, filed as PCT/JP93/00940, Jul. 8, 1993 published as WO94/01574, Jan. 20, 1994, abandoned.

[30] Foreign Application Priority Data

Jul. 10, 1992 [JP] Japan .................................. 4-183972

[51] Int. Cl.$^6$ .............................. C12N 15/63; C12N 1/21
[52] U.S. Cl. .................................. 435/172.3; 435/252.3; 435/252.9; 435/320.1
[58] Field of Search .............................. 435/172.3, 252.3, 435/252.9, 320.1

[56] References Cited

FOREIGN PATENT DOCUMENTS

| | | |
|---|---|---|
| 61-81791 | 4/1986 | Japan . |
| 2-286077 | 11/1990 | Japan . |
| 03251172 | 5/1991 | Japan . |

OTHER PUBLICATIONS

Schwarzer and Pühler Biotechnology 9 84–87 (1991) Manipulation of *orynebacterium glutamicum* by Gene Disruption ...
Sasaki, et al., FEMS Microbiol. Rev. 87.17 (Abstr).
Ragout, et al. Biochimie 71 639–644 (1989) Presence of an L(+)–Lactate Dehydrogenase in Cells of *Lactobicillus delbureckii*...
Bernard, et al. FEBS Letters 290 61–64 (1991) Cloning of the D–Lactate Dehydrogenase Gene From *Lactobacillus delbrueckii* ...
Clewell et al.; "Characterization of 3 Plasmid DNA Molecules in a Strain of Steptococcusfaecalis Identification of a Plasmid Determining Erythromycin Resistance"; Journal of Bacteriology; vol. 117, No. 1, 1974, pp. 283–289.

*Primary Examiner*—James Ketter
*Assistant Examiner*—John S. Brusca
*Attorney, Agent, or Firm*—Bacon & Thomas

[57] ABSTRACT

A gene to be integrated is bound to pAMβ1 plasmid to construct an integration plasmid, which is conjugally transferred into chromosomal DNA of a strain of *Lactobacillus delbrueckii* species. Integration of only the objective gene occurs through homologous recombination events (double crossing-over). According to this method, an arbitrary gene can be integrated into chromosomal DNA of a strain of *Lactobacillus delbrueckii* species and the DNA sequence derived from the vector, pAMβ1, can be completely removed. Therefore, the obtained gene integrant is widely applicable to the production of foods, medicines, feeds and the like.

9 Claims, 9 Drawing Sheets

```
                    5'                                    3'

Pr A    AACGTACACATGATAAA
                   T  C  T     C
                      G        G
                      T        T

Pr 1    GGGAATTCGGTACCAACACCAGATCAAGAGC
                   EcoRI  KpnI

Pr 2    AAATGCATAATTGTCCCTCCGTTAT
                   EcoT22I

Pr 3    AAATGCATAATCTAGCCGCTTAGAA
                   EcoT22I

Pr 4    TGACTGCAACTAAACTA

Pr 5    GTTTTTTGAAGCTTCTT

RV      CAGGAAACAGCTATGAC
```

FIG. 4

GENE INTEGRATION INTO CHROMOSOMES OF *LACTOBACILLUS DELBRUECKII* SPECIES AND INTEGRANTS THEREOF

This application is a Continuation of application Ser. No. 08/193,055, filed Mar. 4, 1994, now abandoned, which is a national stage application of PCT/JP93/00940, filed Jul. 8, 1993 published as WO94/01574, Jan. 20, 1994.

TECHNICAL FIELD

The present invention relates to a method of gene integration into chromosomal DNA of strain of *Lactobacillus delbrueckii* species which are useful for the food industry, to integrants thereof, and also to the use of the integrants.

BACKGROUND ART

*Lactobacillus (Lb.) delbrueckii* species includes *Lb. delbrueckii* subspecies (subsp.) *bulgaricus* and *Lb. delbrueckii* subsp. *lactis*, which have been used in the production of fermented dairy products, such as yogurt and cheese; *Lactobacillus (Lb.) delbrueckii* species also includes *Lb. delbrueckii* subsp. *delbrueckii*, which is used for the production of lactic acid, etc. These three subspecies are very useful industrial lactic acid bacteria. Especially, *Lb. delbrueckii* subsp. *bulgaricus*, together with *Streptococcus salivarius* subsp. *thermophilus*, is a lactic acid bacterium essential for the production of yogurt, and has been used for the production all over the world.

If characteristics of *Lb. delbrueckii* species are improved or given a new character by gene manipulation, the industrial usefulness of this species will be much increased.

For example, *Lb. delbrueckii* metabolizes sugar to generate lactic acid, which is D-lactic acid and is optically different from L-lactic acid generated in the bodies of mammals such as human beings. In the application to foods, the L-type lactic acid is preferable which is the same type of a lactic acid generated in human beings. (Of course, the level of D-lactic acid contained in fermented dairy products, such as yogurt, which people usually consume certainly gives no harm to the health.) Furthermore, if it would be possible to give phage resistance to the lactic acid bacteria, phage contamination should be prevented; if properties of lactic acid bacteria, such as protease activity and lactose utilization, would be controlled at a gene level, the fermentation rate might be improved, and the fermented products with different characteristics from the conventional ones should be obtained. Both flavor improvement and the production of sweet proteins/peptides would be attained by the use of *Lb. delbrueckii* species. In addition, it would be possible to get lactic acid bacteria which produce physiological activators (such as enzymes, hormones and vaccines) useful to human beings which function as medicines in the intestinal tract.

Genetic research of lactic acid has rapidly progressed recently; breeding and improvement of useful lactic acid bacteria by gene manipulation have been intensely studied, in particular, focusing on *lactococci* used in cheese production. In *Lactococcus lactis* species, various vectors and hosts deficient in restriction-modification system have been already developed; efficient transformation systems have been established; the expression of heterologous genes has been reported (Literature 1).

For industrial application, various attempts to stabilize a gene have been made by inserting the objective gene into chromosomal DNA. A homologous recombination using, for example, a part of chromosomal DNA or an insertion element has been reported. Based on this recombination and as a result of application thereof, it has been reported that protease gene was integrated into a chromosome (Literature 2), and that a gene was inactivated by double crossing-over (Literature 3). However, by conventional procedures reported hitherto, selective marker genes (e.g. antibiotic resistance) and the region needed for replication derived from bacteria other than lactic acid bacteria were included in the integration vectors, therefore the application to foods are not expected.

Recently, it has been revealed that a lactose plasmid derived from a Lactococcus strain became unstable at a high temperature, and was integrated into chromosomal DNA depending on strains, and the plasmid was studied as an integration vector applicable to foods (Literature 4).

Efficient transformation systems have been reported for some *lactobacilli*, and foreign genes were integrated into the chromosomal DNA of one strain and were expressed (Literature 5).

So far, however, no recombinant (integrant) has been reported which was obtained by integrating a useful gene into chromosomal DNA in order to stabilize its character, which is thought to be safe at the food level, so that a new approach has been desired to solve these problems.

Compared with those advanced researches shown above, genetic researches of *Lb. delbrueckii* species stay behind, and only a few cases of gene transfer have been reported.

The present inventors have recently reported that, when pAMβ1 plasmid was conjugally transferred to all three subspecies of *Lactobacillus delbrueckii* (Literature 6), the plasmids were integrated into chromosomal DNA without replicating as a plasmid (Literature 7). Based on the disclosure of these reports, *Lactobacillus delbrueckii* species is expected to be bred and improved from now on. In particular, the phenomenon that pAMβ1 is integrated into chromosomal DNA of *Lb. delbrueckii* species is considered to be applicable to the stabilization of useful genes. However, since it is difficult to deal with pAMβ1 because of its large size, there have been no reports that a foreign gene was inserted into pAMβ1 by in vitro manipulation or the plasmid was used as a vector. Moreover, as pAMβ1 has an ability to transfer conjugally and an antibiotic resistance gene, the plasmid is not suitable for the application to foods when pAMβ1 is used as a vector and integrated into chromosomal DNA.

To establish safety is the most important issue for application to foods if improving the characteristics of *Lb. delbrueckii* species is intended by means of transformation or conjugal transfer. For this purpose, any improved strain of *Lb. delbrueckii* species must be composed, at the very least, of only the elements (strains/genes/DNA) which have been confirmed to be safe.

In addition, to be suited for the industrial application, it is important that the improved *Lactobacillus delbrueckii* species be stable, and that characteristics of the strain except the improved one(s) be not inferior to those of the original host.

The purpose of this invention, therefore, is to integrate the useful genes in mind into chromosomal DNA of *Lb. delbrueckii* species to stabilize the genes, and to establish a method to secure the safety and the industrial usefulness.

DISCLOSURE OF THE INVENTION

The present invention provides a method of integrating a gene into the chromosomal DNA of *Lactobacillus delbrueckii* species, comprising the following three steps:

Step 1: two genomic DNA fragments on both sides of the site to be integrated on the chromosomal DNA of Lactobacillus delbrueckii species are ligated at upstream and downstream, respectively, of a gene to be integrated, and inserting this ligated DNA fragment into a vector, pAMβ1 plasmid, to construct an integration plasmid;

Step 2: introducing the constructed plasmid into a strain of Lactobacillus delbrueckii species by conjugal transfer method to obtain transconjugants exhibiting erythromycin resistance by integration to the chromosomal DNA;

Step 3: repeating subculture of the obtained transconjugants under non-selective conditions in the absence of erythromycin, selecting clones which have become sensitive to erythromycin as a result of losing the DNA sequence derived from pAMβ1 plasmid by homologous recombination, and finally, from the erythromycin sensitive clones obtained, selecting gene integrants in which the gene to be integrated remains in the chromosomal DNA of the strain of Lactobacillus delbrueckii species.

BRIEF DESCRIPTION OF DRAWINGS

FIG. 4 shows nucleotide sequences of oligonucleotides.

Sequence PrA is a nucleotide sequence corresponding to the 15th through, the 20th amino acid sequence of the partial peptide of D-lactate dehydrogenase of M-878 strain of Lactobacillus delbrueckii subsp. bulgaricus (LB-LDH). Duplicated nucleotides are listed vertically. Thus there are sixty-four variations of the nucleotide sequence for PrA. Four variations are illustrated in SEQ ID NOS. 2,3,4 and 5.

Sequence Pr1 (SEQ ID NO.6) comprises the sequences of recognition sites of EcoRI and KpnI and a sequence from the 7th to the 23rd nucleotide of LB-LDH gene (Table 1).

Sequence Pr2 (SEQ ID NO.7) comprises the sequence of a recognition site of EcoT22I and a complementary sequence from the 344th to the 360th nucleotide of LB-LDH gene.

Sequence Pr3 (SEQ ID NO.8) comprises the sequence of a recognition site of EcoT22I and a sequence from the 1361st to the 1377th nucleotide of LB-LDH gene.

Sequence Pr4 (SEQ ID NO.9) comprises a sequence from the 1852nd to the 1868th nucleotide (Japanese Patent Application Laid-Open (kokai) No. 251172/1991) of L-lactate dehydrogenase gene derived from M-192 strain of Streptococcus salivarius subspecies thermophilus.

Sequence Pr5 (SEQ ID NO.10) comprises a complementary sequence from the 2817th to the 2834th nucleotide of the same.

RV (SEQ ID NO.11) is a nucleotide sequence of M13 primer RV (by Takara Shuzo).

Figure 5:
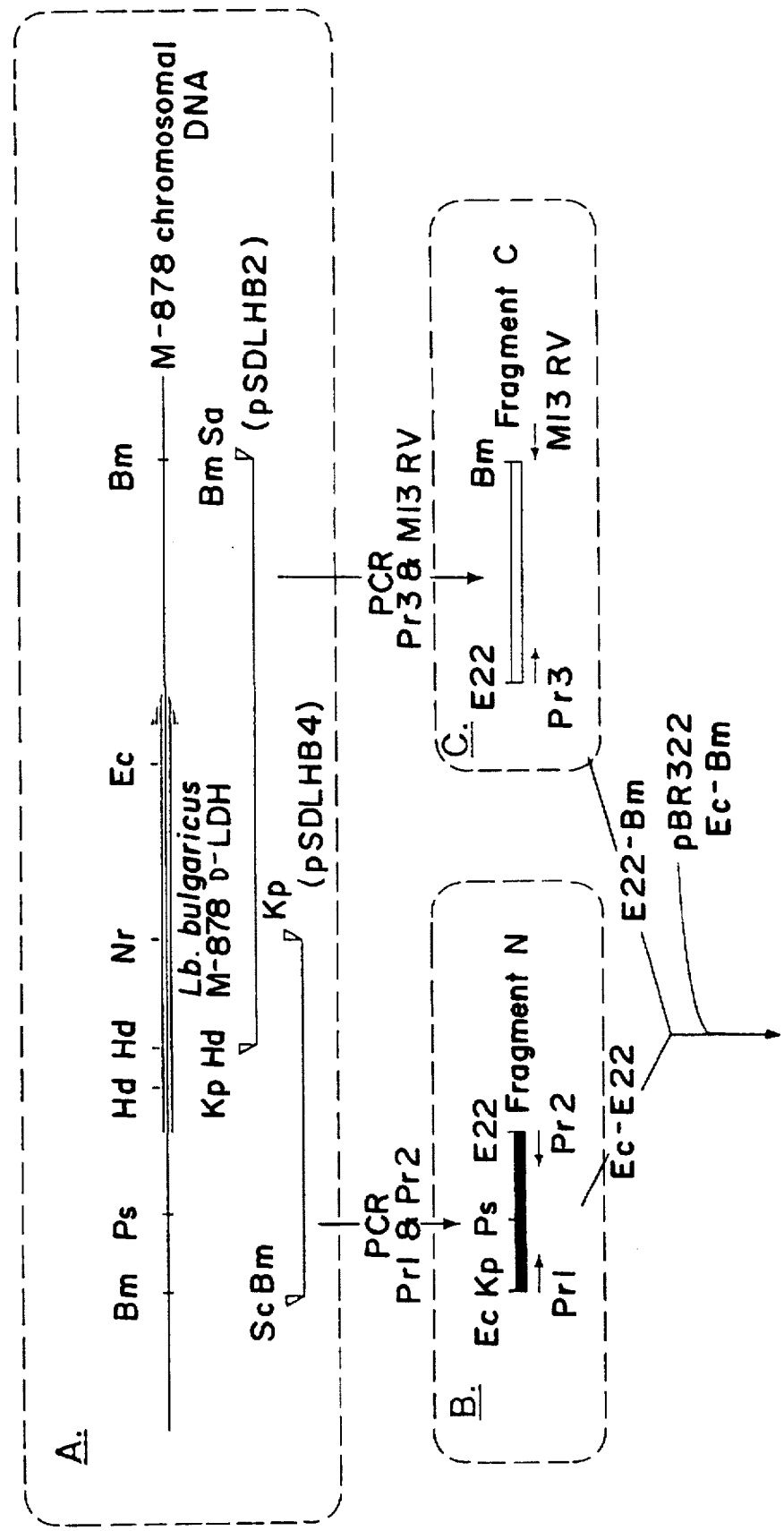

FIGS. 5A–C shows a partial process in the course of the construction of pβL-Int1 and pβL-Int2.

A: a restriction enzyme map showing around the D-lactate dehydrogenase (LB-LDH) gene of M-878 strain of Lactobacillus delbrueckii subsp. bulgaricus, and fragments included in pSDLHB2 and pSDLHB4.

B: Fragment N which is a 5'-non-translational region of LB-LDH gene.

C: Fragment C which is a 3'-non-translational region of LB-LDH gene.

FIGS. 6D–G shows a partial process in the course of the construction of pβL-Int1 and pβL-Int2.

D: a restriction enzyme map of pBRLD13.

E: Fragment L which is a structural gene of L-lactate dehydrogenase;(ST-LDH) from Streptococcus salivarius subspecies thermophilus M-192 strain.

F: a restriction enzyme map of pBRLD21.

G: a restriction enzyme map of p8Em1.

FIGS. 7H–I shows a partial process in the course of the construction of pβL-Int1 and pβL-Int2.

H: a restriction enzyme map of pBLEm211.

I: a restriction enzyme map of pAMβ1.

Figure 7:
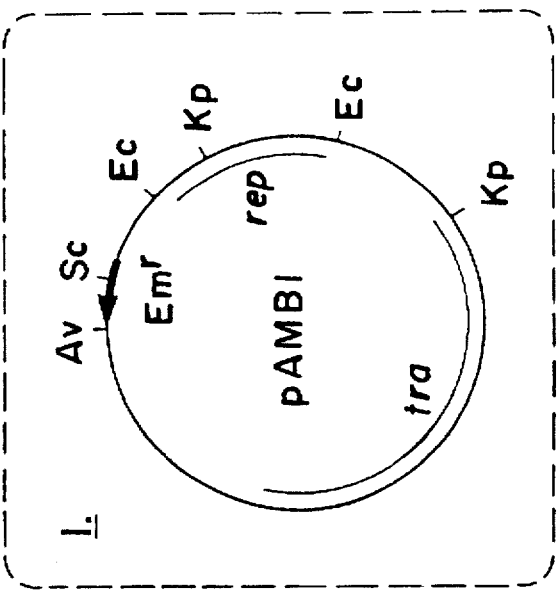
Figure 7:
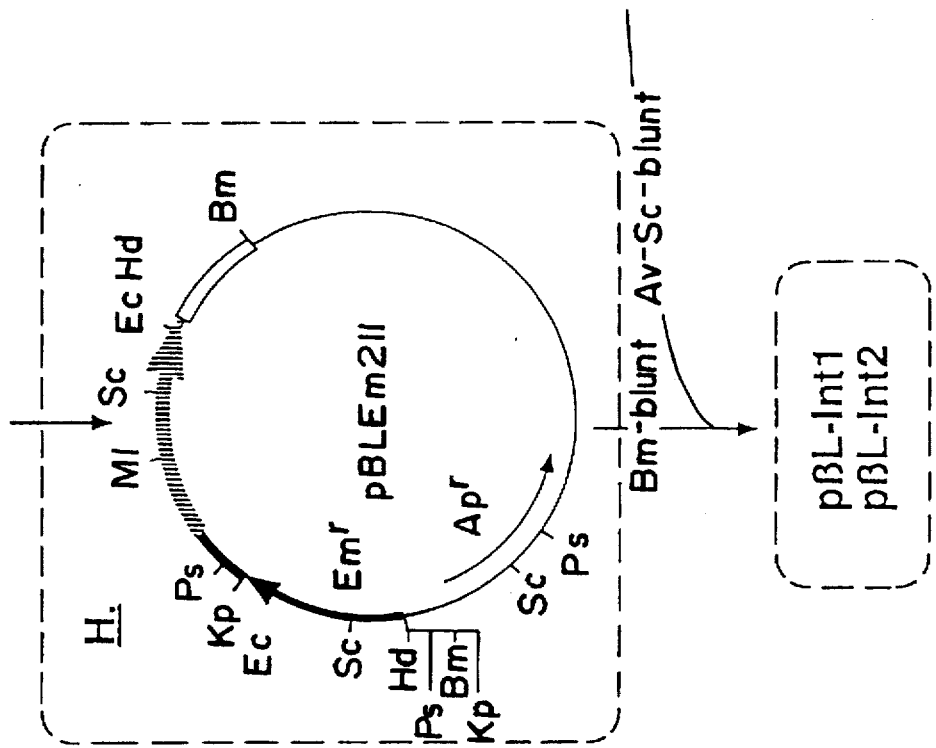

In FIG. 7, an arrow with lateral stripes shows the structural gene of LB-LDH; a black square shows a 5'-non-translational region of LB-LDH; a white square shows a 3'-non-translational region of LB-LDH; an arrow with vertical stripes shows the structural gene of ST-LDH; arrows with bold line (Emr) shows an erythromycin resistance gene derived from pAMβ1 and the transcriptional direction; an arrow with fine line (Apr) shows an ampicillin resistance gene and the transcriptional direction; a straight arrow shows an oligonucleotide primer and its direction from 5'-end to 3'-end; rep shows a replicative region of pAMβ1; tra shows a region needed for conjugal transfer of pAMβ1.

Figure 8:
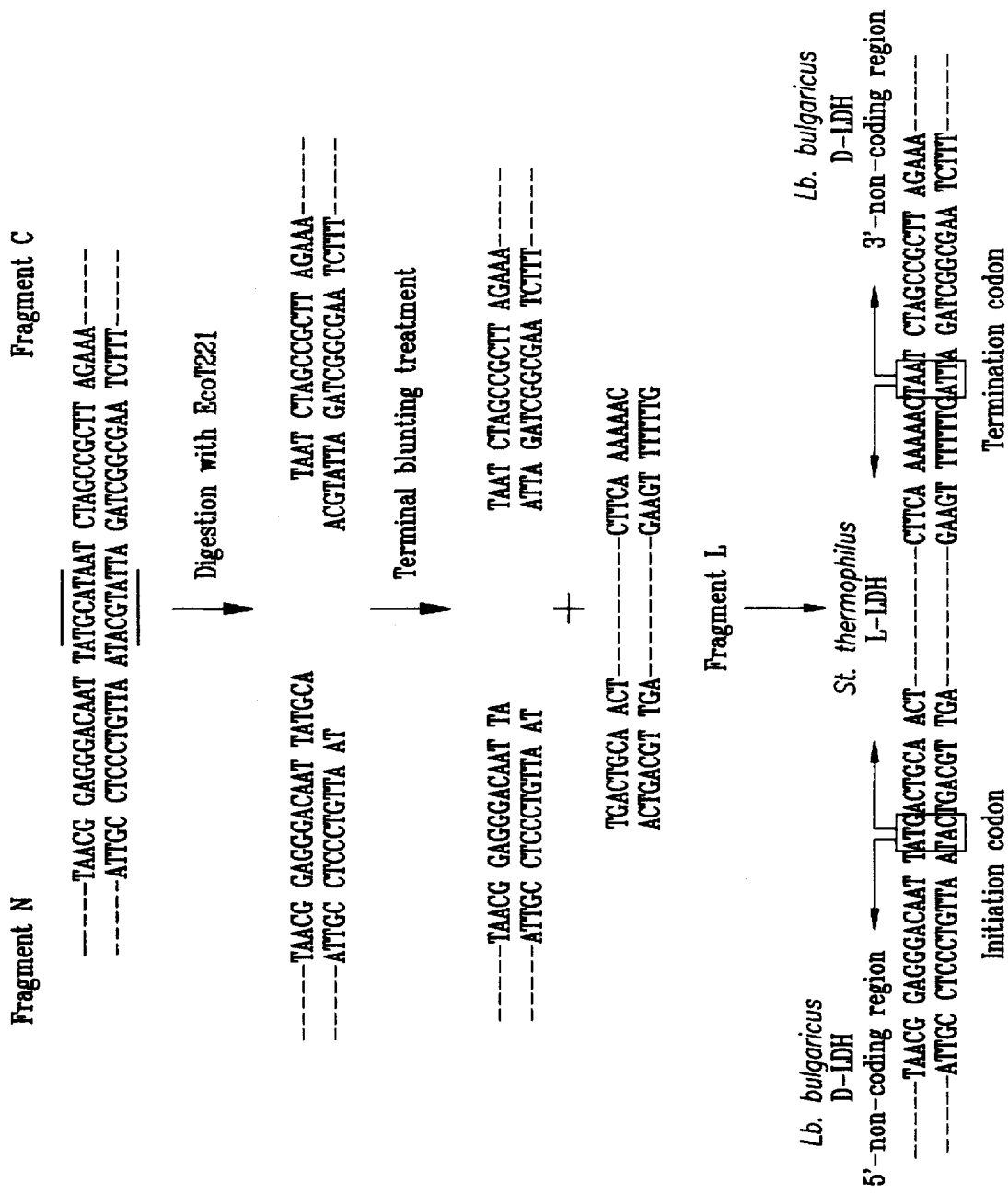

FIG. 8 shows a process of ligation Fragment L (the top strand of which is shown by SEQ ID NOS. 17 and 18) to Fragments N and C (the top strands of which are shown by SEQ ID NOS. 15 and 16 respectively). The sequence shown at the bottom of the Figure (the top strand of which is shown by SEQ ID NOS. 19 and 20) is a nucleotide sequence obtained by ligation. (Initiation and termination codons of L-lactate dehydrogenase gene of M-192 of Streptococcus salivarius subsp. thermophilus regenerated by ligation are respectively shown in squares.)

FIG. 8 illustrates a process in which the fragment shown at the top of the figure (the top strand of which is shown by SEQ ID NO. 12) is digested with Ecot22I to produce fragments N and C prior to terminal blunting treatment. The top strand of fragments N and C (prior to the terminal blunting treatment) are shown in SEQ ID NOS. 13 and 14 respectively. The terminal blunting treatment produces blunt ends on fragments N and C. The blunt ended fragments N and C have nucleotide sequences, the top strands of which are shown in SEQ ID NOS. 15 and 16.

Figure 9:
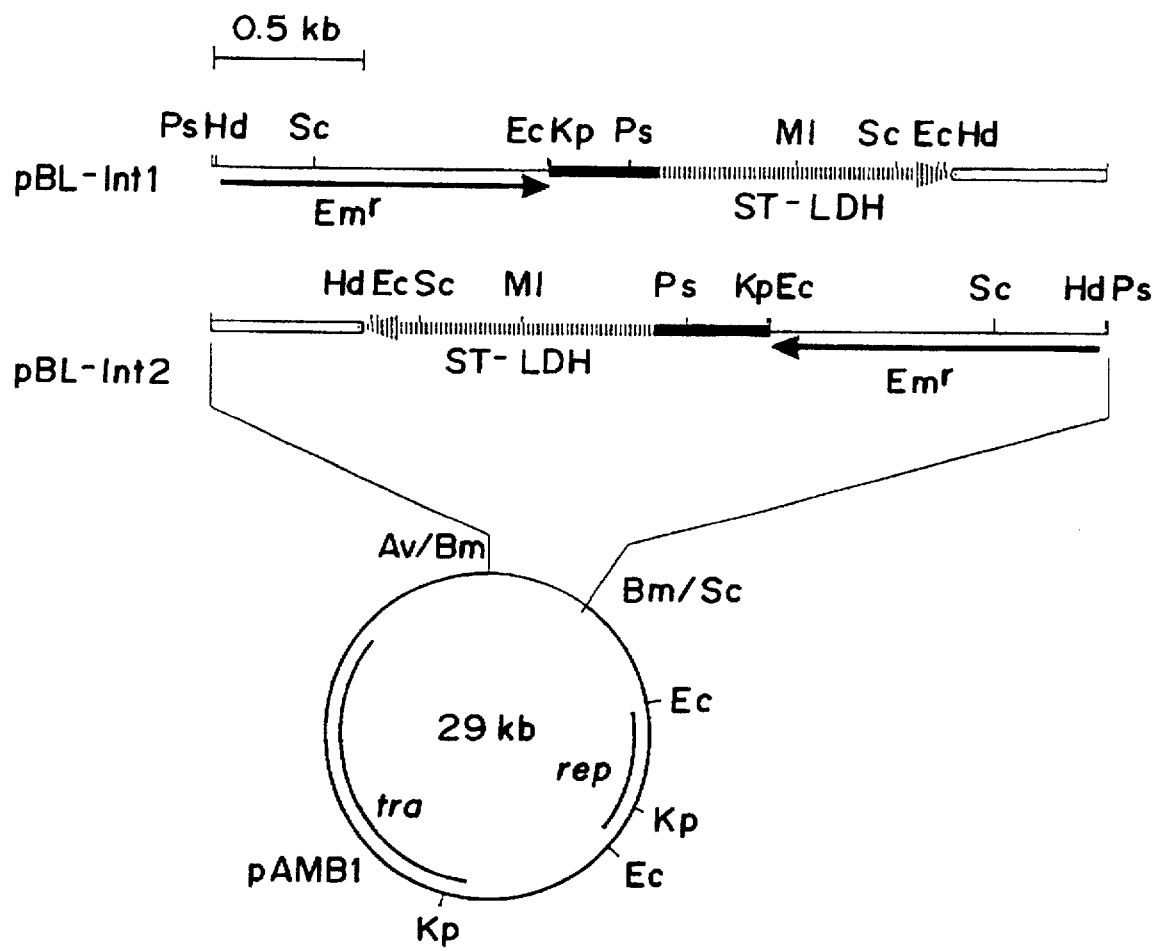

FIG. 9 shows restriction enzyme maps of pβL-Int1 and pβL-Int2. In FIG. 9, an arrow with lateral stripes shows a structural gene of D-lactate dehydrogenase of M-878 strain of Lactobacillus delbrueckii subsp. bulgaricus; a black square shows a 5'-non-translational region thereof; a white square shows a 3'-non-translational region thereof; an arrow with vertical stripes shows the structural gene of L-lactate dehydrogenase of M-192 strain of Streptococcus salivarius subsp. thermophilus; an arrow with bold line (Emr) shows an erythromycin resistance gene derived from pAMβ1 and its transcriptional direction; rep shows a replicative region of pAMβ1; tra shows a region needed for conjugal transfer of pAMβ1.

The symbols in FIG. 9 stand for as follows:
Av: AvaI
Bm: BamHI
Ec: EcoRI
E22: EcoT22I
Hd: HindIII
Kp: KpnI
Ml: MluI
Nr: NruI
Ps: PstI
Sc: ScaI

BEST MODE FOR CARRYING OUT THE INVENTION

Step 1: Construction of "Integration Plasmid"

To achieve the objective, a useful gene must be integrated to the objective site of chromosomal DNA of *Lactobacillus delbrueckii* species. Namely, a plasmid available for a vector must have a conjugal transfer activity, have a selective marker, and must be integrable into chromosomal DNA of *Lactobacillus delbrueckii* species. For example, pAMβ1 plasmid which has already been known to be integrable into a chromosome, would be the most suitable as such a vector. Among others, pIP501 having conjugal transfer activity and a lactose plasmid may also be used (Literature 14).

A case where a pAMβ1 plasmid is used as a conjugal transfer plasmid is mentioned. As this plasmid is relatively large (26.5 kb) as described above and has many restriction sites, there is no publication reporting that a recombinant plasmid inserted with an objective gene has been obtained without giving any damage to the resistance against erythromycin (hereinafter may be simply referred to as Em) and conjugal transfer activity. The present inventors bound a DNA fragment of pAMβ1 in which Em resistance gene on pAMβ1 was inactivated, to a combined DNA fragment constructed by ligation of a DNA fragment to be inserted and an Em resistance gene, devised to select only a recombinant plasmid to which the objective DNA fragment was inserted, as having Em resistance, and succeeded to obtain a recombinant plasmid having the objective gene without losing Em resistance and conjugal transfer activity.

For example, when pAMβ1 is digested at AvaI and ScaI sites which are unique restriction sites thereof, a fragment including a part of Em resistance gene is removed; however, the replicative region of the plasmid and the region for controlling conjugal transfer activity are kept intact in the residue of about 26 kb of DNA fragment. This DNA fragment after AvaI and ScaI digestion is blunt-ended; the blunt-ended fragment is ligated with the fragment which contains an objective gene and an Em resistance gene after blunt-end reaction; if the ligated fragment is transformed into an appropriate host, a clone harboring the objective recombinant plasmid can be selected from transformants having Em resistance. No particular limitation is imposed on the host for constructing a recombinant plasmid, as long as pAMβ1 can be replicated and transformation efficiency is satisfactory as is a strain which lacks its restriction and modification system. For example, Gram-positive bacteria, such as RM-215 strain of *Bacillus subtilis* and *lactococcus* strains (for example, MG1363 strain of *Lactococcus lactis* subspecies *lactis*), can be used. Next, in order to enable application to foods, a nucleotide sequence derived from the vector, pAMβ1, is required to be removed. For doing this, it is necessary to construct a recombinant plasmid in which unnecessary nucleotide sequences can be removed by homologous recombination.

Figure 1:
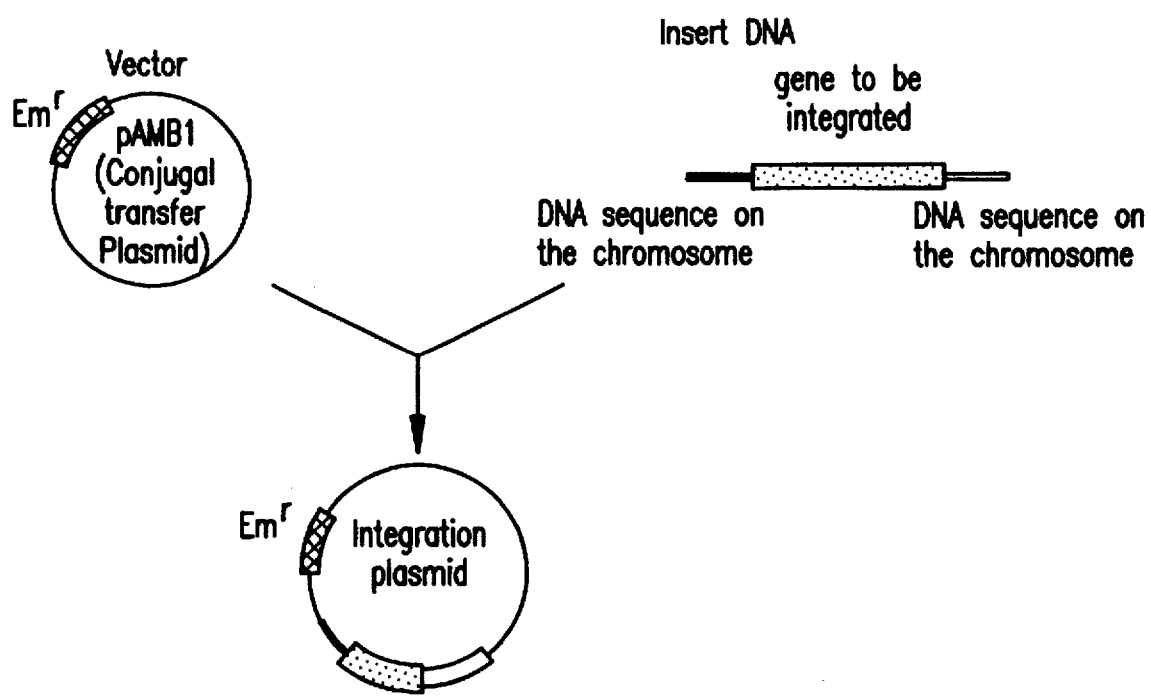
FIG. 1 is a schematic diagram of the first step of the method of gene integration into the chromosomal DNA of Lactobacillus delbrueckii species according to the present invention.

In other words, to integrate a gene into an objective site on chromosomal DNA of *Lactobacillus delbrueckii* species, genomic DNA fragments of both sides (upstream and downstream) of the site (or DNA fragments having nucleotide sequences with high homology to these fragments) are prepared; the two genomic DNA fragments are ligated at the upstream and downstream (or vice versa) of the gene; after an Em resistance gene is ligated to this combined fragment, a recombinant plasmid is constructed by ligation to the pAMβ1 plasmid vector which lacks an Em resistance gene by the aforementioned procedure or the like (FIG. 1).

As the recombinant plasmid constructed as above has two nucleotide sequences homologous to the host chromosomes, when homologous recombination arises twice (double crossing over), the selective marker gene and DNA sequences from pAMβ1 vector are completely removed, so that a gene integrant, in which only the objective gene is integrated into chromosomal DNA, can be obtained.

The two genomic DNA fragments can be freely selected according to the purposes. In the case where a specific gene on chromosomal DNA of *Lactobacillus delbrueckii* is substituted by another gene or is inactivated, it is suitable to use upstream and downstream genomic DNA fragments of the gene. If a gene is simply desired to be integrated on chromosomal DNA of *Lactobacillus delbrueckii* species, multiple copy genes, such as rRNA gene, and genomic DNA fragments in a spacer region between genes are selected so that the gene essential for growth of *Lactobacillus delbrueckii* species may not be inactivated.

These recombinant plasmids are hereinafter referred to as an "integration plasmid". That is, an "integration plasmid" is constructed from a conjugal transfer plasmid as a vector, has chromosomal DNA fragments of *Lactobacillus delbrueckii* species in front of and behind the objective gene to be integrated and can cause recombination at a homologous site on the chromosomal DNA.

Step 2: Conjugal Transfer to *Lactobacillus delbrueckii* Species and Integration into Chromosome The transformant obtained in Step 1 can be used as a donor harboring an "integration plasmid". If transconjugants of *Lactobacillus delbrueckii* species are not available because the frequency of conjugal transfer is low, it is effective to transfer the "integration plasmid" from the relevant transformant to a strain with high conjugal transfer frequency (e.g. *Lactococcus lactis*) by a conjugal transfer method in order to use the obtained transformant as a donor.

To transfer the objective "integration plasmid" conjugally to a recipient *Lactobacillus delbrueckii* species, a method developed by the present inventors is suitable (Literature 7), in which a filter method (Literature 9) is applied and a culture medium containing polyethylene glycol is used for a mixed culture (the process of conjugal transfer) of donor and recipient cells.

A transconjugant can be selected using Em resistance as a marker. Whether a strain is a transconjugant or not can be determined by its character, Em resistance and so on which are investigated by ordinary microbiological methods. After the introduced "integration plasmid" is confirmed not to replicate as a plasmid, chromosomal DNA is analyzed by Southern hybridization method, and thus the relevant plasmid is confirmed to be integrated into the chromosomal DNA.

Figure 2:
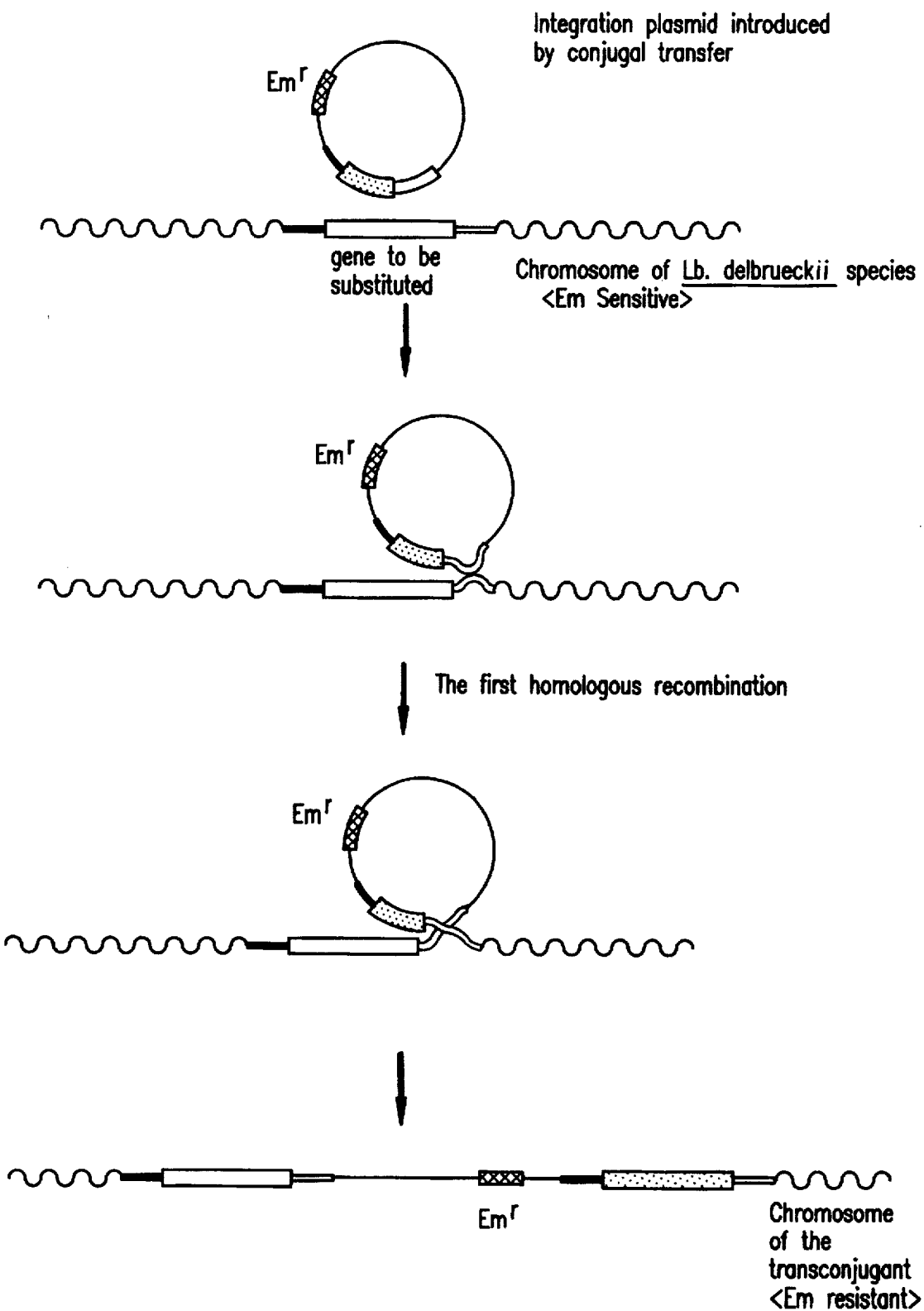
FIG. 2 is a schematic diagram of the second step of the method of gene integration into the chromosomal DNA of Lactobacillus delbrueckii species according to the present invention.

The "integration plasmid" constructed in Step 1 includes two chromosomal DNA fragments. It is, therefore, considered that in most transconjugants the relevant plasmid is integrated into chromosomal DNA by the first recombination at either site (homologous sequence) of the two regions (FIG. 2).

Step 3: Removal of Useless Genes by the Second Homologous Recombination

The chromosomal DNA of the transconjugant obtained by the above steps harbors not only the objective gene but also useless genes derived from the vector pAMβ1. The transconjugant itself, therefore, is not suitable for application to foods, and those useless genes must be removed by homologous recombination.

The principle of the removal is to select a clone in which the DNA nucleotide sequence sandwiched between the two homologous regions in the "integration plasmid" inserted in the Step 2 (FIG. 3) is removed by the second recombination with the chromosomal DNA at the other homologous region.

When a transconjugant, which the "integration plasmid" is integrated into, is subcultured repeatedly in the absence of Em, clones which have lost DNA fragments including sequences derived from pAMβ1 by the second homologous recombination are found at a detectable frequency. Thus, after transconjugants are subcultured in a skim milk or MRS medium in the absence of Em, many single colonies are isolated and sensitive clones to Em are obtained. If the passage number and the number of colonies to be investigated are increased, it is possible to obtain Em sensitive clones, in which the objective clone still remains. These clones have no DNA sequences originated from pAMβ1. A clone, which is obtained by integrating an objective gene into a chromosome of *Lactobacillus delbrueckii*, and which does not hold a DNA sequence originated from pAMβ1, is hereafter referred to as a "gene integrant".

The "gene integrant" has the following characteristics:

(1) The objective gene is stably retained as it is integrated into the chromosomal DNA. This eliminates the fear of dropping out the objective gene which may occur when it is introduced using a replicative plasmid vector.

(2) If genes to be introduced are limited to those creatures employed for food production, no genes of pAMβ1 remain in the "gene integrant", and since the genes introduced to chromosomal DNA are derived from creatures used for the production of foods, the "gene integrant" is composed only of safe genetic elements, the safety may be ensured and the application of the "gene integrant" to foods may be possible.

(3) Because of the fact that only the gene newly integrated into the chromosome of the "gene integrant" is different from the genetic composition of the original *Lactobacillus delbrueckii* species, new character can be given to *Lactobacillus delbrueckii* species without losing any of the original characteristics only when integration sites are selected suitably. Accordingly, since the industrially useful characteristics will not be damaged or lost, the industrial applicability of the "gene integrant" can be secured.

Various "gene integrants" can be created, depending on the kinds of genes to be integrated or on the selection of DNA fragments of two homologous regions of chromosomal DNA.

By using the method as described, a specified gene in chromosomal DNA can be substituted by another gene. As an application of this, for example, a *Lactobacillus delbrueckii* species, which generates L-lactic acid but no D-lactic acid, can be obtained by substituting a foreign L-lactate dehydrogenase gene for the D-lactate dehydrogenase gene of *Lactobacillus delbrueckii* species.

Further, if a relevant gene on chromosomal DNA of *Lactobacillus delbrueckii* species is substituted as described above after constructing an "integration plasmid" with the DNA fragment lacking a part of the specified gene on the chromosomal DNA, a clone of the *Lactobacillus delbrueckii* species deficient in the specified gene can be obtained. In a similar manner, a host with high transformation efficiency can be developed, because a variant of *Lactobacillus delbrueckii* deficient in a restriction-modification system can be gained.

Moreover, it is possible to add a foreign gene, which is not present in *Lactobacillus delbrueckii* species, to the chromosomal DNA of the species. Thus, new useful characters, such as production of sweet proteins and enzymes useful in the food industry, can be given to *Lactobacillus delbrueckii* species.

The number of gene copies to be integrated may be 1; however, multiple copies of the gene may be integrated into chromosomal DNA for increasing the expression of the relevant gene.

EXAMPLES

The present invention will now be described by way of examples hereunder, which however should not be construed as limiting the invention thereto.

Example 1. Purification of D-Lactate Dehydrogenase and Determination of Partial Amino Acid Sequence M-878 strain of *Lactobacillus delbrueckii* subsp. *bulgaricus* (deposited with Fermentation Research Institute, Agency of Industrial Science and Technology as the Deposition No. FERM BP-3758; may be simply referred to as M-878) was cultivated in a LCMG culture medium which was prepared by adding 1% of glucose to a LCM culture medium (Literature 10), at 37° C. overnight. The cultivated cells were fractured by ultrasonic treatment, and the cell debris were removed by centrifugation. D-lactate dehydrogenase (may be simply referred to as LB-LDH) was obtained and purified. One unit of enzyme activity was defined to be equal to the quantity of the enzyme which converts 1 μmole of reduced nicotinamide adenine dinucleotide into an oxidized form per minute in a reaction mixture containing 50 mM of Tris-hydrochloric acid buffer solution (pH 7.5), 5 mM of pyruvate, and 0.2 mM of reduced nicotinamide adenine dinucleotide. LB-LDH was purified until a single band was exhibited in SDS-polyacrylamide gel electrophoresis (according to Literature 11), by DEAE cellulose (Whatman) column chromatography (pH 5.5), by phenylsepharose (Pharmacia) column chromatography (pH 5.5) and by MONO Q HR5/5 column (Pharmacia) high performance liquid chromatography (pH 7.0). Table 1 shows the purification process from 20 g cells (wet weight).

TABLE 1

| | Sample volume (ml) | Total activity (unit) | Specific activity (unit/1 mg of protein) | Magnification of purification | Yield (%) |
|---|---|---|---|---|---|
| Crude cell extract | 58 | 10560 | 4.55 | 1 | 100 |
| DEAE-Cellulose | 6.5 | 14130 | 65.5 | 14.4 | 133.9 |
| Phenylsepharose | 1 | 12400 | 218.3 | 48.0 | 117.5 |
| Mono Q (partial) | 0.06 | 130 | 219 | 48.1 | (31) |

About 1 μg of the purified LB-LDH was incubated with lysyl endopeptidase (Sigma) at 37° C. for 16 hours in the presence of 4M of urea. The obtained peptide fragments were separated by high performance liquid chromatography using a $C_8$ hydrophobic column (Toyo Soda). The obtained partial peptides of LB-LDH were submitted to an amino acid sequencer to determine the amino acid sequences. One of the amino acid sequences was Gln-Ala-Asp-Val-Ile-Ser-Leu-His-Val-Pro-Asp-Val-Pro-Ala-Asn-Val-His-Met-Ile-Asn (unreadable thereunder).

Example 2. Preparation of Homologous Sequences

Mixed oligonucleotide (hereinafter may be referred to as PrA) was synthesized (FIG. 4) to include all the nucleotide sequences having the possibility of corresponding to the 15th to 20th sequence (Asn-Val-His-Met-Ile) of the amino acid sequence shown in Example 1. For the synthesis, a DNA Synthesizer 380A-Type of Applied BioSystems was used.

Chromosomal DNA was prepared from M-878 strain by a method based on that of Saito and Miura (Literature 8). Southern hybridization experiments were performed according to a conventional method (Literature 13) with the chromosomal DNA of M-878 using PrA as a probe. The PrA probe specifically hybridized to the fragment of about 1400 base pairs (bp) of the chromosomal DNA digested with HindIII and BamHI.

After digestion with HindIII and BamHI of the chromosomal DNA of M-878, and agarose gel electrophoresis according to a conventional method, only the region including about 1400 bp fragments was cut out and DNA was recovered with the GeneClean DNA purification kit from BIO101. The recovered DNA fragments were ligated to the *Escherichia coli* plasmid pBluescriptSK+ (Toyobo) which had been digested with HindIII and BamHI, to transform *Escherichia coli* TG1 (Amersham). Colonies obtained were colony-hybridized and selected using PrA probe according to a conventional method (Literature 13), to obtain a plasmid pSDLHB2 containing a part of LB-LDH gene (FIG. 5A).

The DNA nucleotide sequence of the part of the chromosomal DNA from M-878 inserted into pSDLHB2 was determined by using the Kilo Sequence Kit (Takara Shuzo) and a Sequenase ver 2.0 7-deaza sequencing kit (United States Biochemical). It was revealed that the sequence contained a nucleotide sequence corresponding to the amino acid sequence for a partial peptide of the LB-LDH shown in Example 1.

Southern hybridization was conducted using, as a probe, about 250 bp DNA fragment of pSDLHB2 obtained by digestion with NruI and HindIII. As a result, among the chromosomal DNA fragments of M-878 digested with NruI and BamHI, a fragment of about 800 bp specifically hybridized. This fragment was cloned in pBluescriptSK+ digested with HincII and BamHI in a similar manner as applied to pSDLHB2, and a plasmid pSDLHB4 was obtained (FIG. 5A). The nucleotide sequence of DNA fragment inserted into pSDLHB4 was determined in the same way.

Sequence No. 1 shows the nucleotide sequence of the entire LB-LDH gene determined by the DNA sequences obtained from the inserted fragments in pSDLHB4 and pSDLHB2. The structural gene of LB-LDH corresponds to the open reading frame (ORF) from the 361st A to the 1362nd A of the nucleotide sequence as shown in Sequence No.1. The DNA fragment inserted into pSDLHB2 corresponds to the C-terminal part of LB-LDH and a 3'-non-translational region; The DNA fragment inserted into pSDLHB4 corresponds to the N-terminal part of LB-LDH and a 5'-non-translational region. The partial amino acid sequence obtained in Example 1 corresponds to the amino acid sequence coded by the nucleotide sequence from the 955th C to the 1014th C of Sequence No. 1 and PrA matched with the nucleotide sequence from the 997th to the 1013rd of Sequence No. 1. Compared to the D-lactate dehydrogenase gene of LMG6901 strain of *Lactobacillus delbrueckii* subsp. *bulgaricus* (LMG6901 strain) reported in Literature 14, it was revealed that the present LB-LDH and D-lactate dehydrogenase of LMG6901 strain differed in 6 sites in the nucleotide sequence of the structural gene, which resulted in three different amino acid residues.

Based on the determined nucleotide sequence of LB-LDH gene, oligonucleotides Pr1, Pr2 and Pr3 (FIG. 4) were synthesized. Using about 1 ng of pSDLHB4 as a substrate, Pr1 and Pr2 as primers, and also using AmpliTaqDNA Polymerase (Cetus), the primer chain reaction (PCR) was performed under the following conditions. Forty μl of mineral oil (Sigma) was overlaid on 50 μl of a reaction mixture containing 50 mM of KCl, 10 mM of Tris buffer solution (pH 8.4), 2.5 mM of MgCl$_2$, 200 μM of dATP, 200 μM of dCTP, 200 μM of dGTP, 200 μM of TTP, 200 μg/ml of gelatin, 1 μM of primers (Pr1 and Pr2), and 5 units of AmpliTaqTM DNA polymerase. A cycle of incubation at 94° C. for 1 min., at 55° C. for 1 min., and at 72° C. for 2 min. was repeated 25 times. As a result, about 370 bp of DNA fragment was amplified specifically. This fragment was designated Fragment N (FIG. 5B). Fragment N corresponds to the 5'-non-translational region of the LB-LDH gene.

Another PCR was performed using about 1 ng of pSDLHB2 as a substrate and Pr3 and M13 Universal RV Primer (FIG. 4; Takara Shuzo) as primers. As a result, about 590 bp of DNA fragment was amplified and designated Fragment C (FIG. 5C). Fragment C corresponds to the 3'-non-translational region of the LB-LDH gene.

Figure 6:
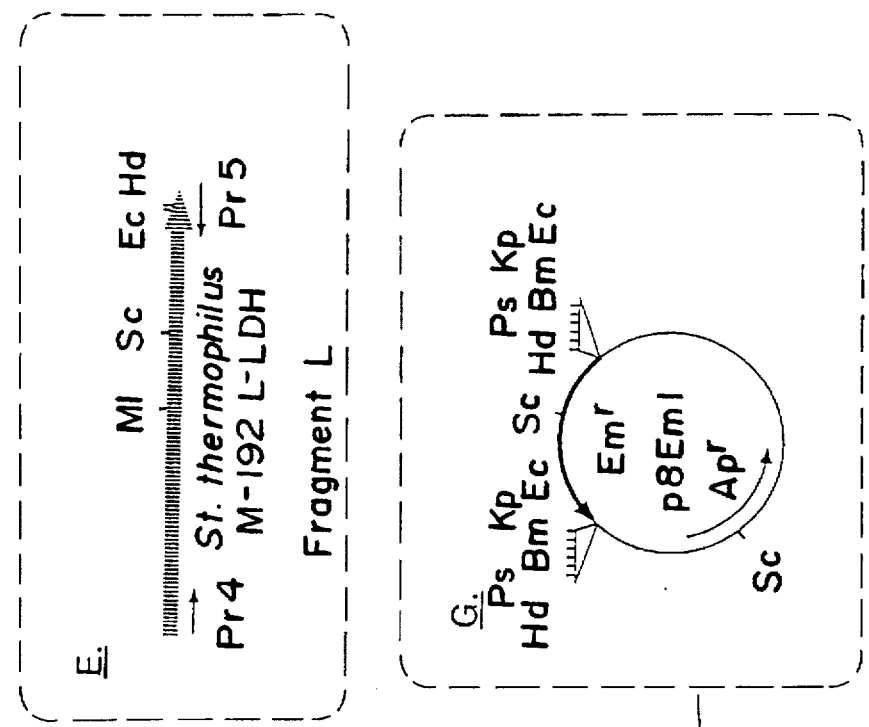
Figure 6:
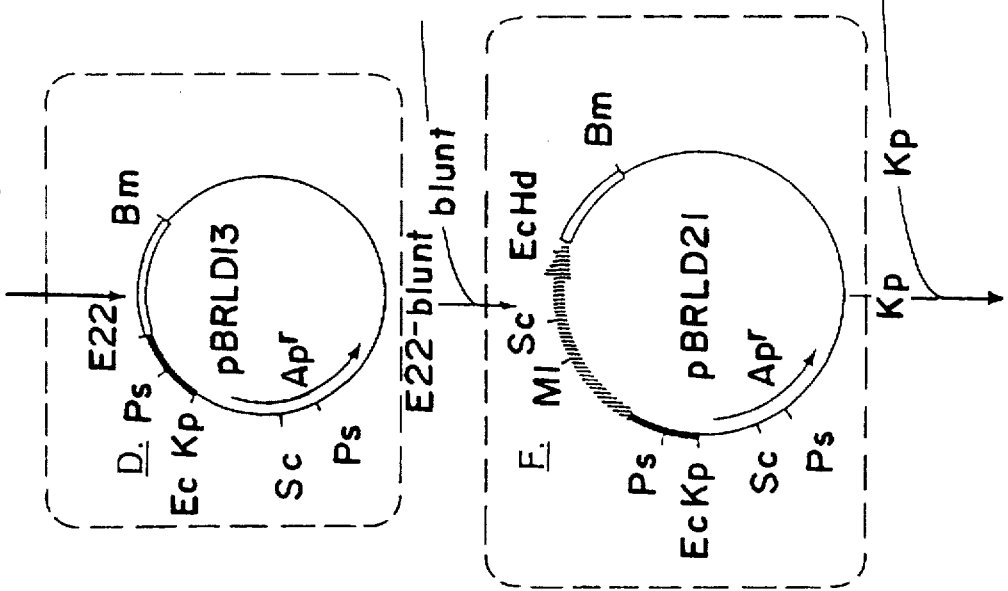

The amplified DNAs of Fragments N and C were separated by agarose gel elecrophoresis and cut out. The recovered Fragment N was digested with restriction enzymes EcoRI and EcoT22I. The recovered Fragment C was digested with BamHI and EcoT22I. These two fragments were ligated to pBR322 plasmid (Takara Shuzo) which had been digested with EcoRI and BamHI, to obtain pBRLD13 (FIG. 6D).

Example 3. Binding to L-lactate Dehydrogenase Gene

Oligonucleotides Pr4 and Pr5 (FIG. 4) were synthesized from a DNA nucleotide sequence of the gene coding for an L-lactate dehydrogenase (See Japanese Patent Application Laid-Open (kokai) No. 251172/1991; may be referred to as ST-LDH) derived from M-192 strain of *Streptococcus salivarius* subsp. *thermophilus* (owned by Meiji Institute of Health Science, Meiji Milk Products Co., Ltd.). PCR was performed using these primers and a substrate of *Escherichia coli* plasmid pBEV1 (See Japanese Patent Application Laid-Open (kokai) No. 251172/1991) including ST-LDH gene. About 1000 bp of specifically amplified DNA fragment was obtained (FIG. 6E). This fragment was named Fragment L, which corresponds to a structural gene of ST-LDH.

The amplified Fragment L was cut out from agarose gel, by a similar procedure of Example 2. DNA Fragment L obtained as above was blunt-ended with a DNA Blunting Kit (Takara Shuzo). pBRLD13 plasmid obtained in Example 2 was digested with EcoT22I and blunt-ended in the same way. These blunted DNA fragments were ligated to obtain pBRLD21 (FIG. 6F). The nucleotide sequences of the combined sites of Fragments L with Fragments N and C are shown in FIG. 8. These combinations regenerated the initiation and termination codons of ST-LDH gene, and produced a structure in which only the LB-LDH structural gene of LB-LDH (nucleotide Nos. 361 to 1362) shown in Sequence No. 1 was replaced with the structural gene of ST-LDH (Fragment L).

Example 4. Constitution of pβL-Int Plasmids pBRLD21 obtained in Example 3 was digested with KpnI and ligated with the Em resistance gene (about 1.1 kb of DNA fragment) digested with KpnI from the erythromycin cassette plasmid p8Em1 (FIG. 6G) to obtain pBLEm211 plasmid (FIG. 7H).

Before our trials to use the conjugal plasmid of pAMβ1 (FIG. 7I) originated from *Enterococcus faecalis* as a vector, it was assumed to be difficult to perform recombination due to the fact that pAMβ1 is relatively long and its total length is about 26.5 kb. The present inventors devised a positive selection, based on Em resistance, of the recombinant plasmid which has the insert DNA fragment. This was performed by inactivating the Em resistance gene on pAMβ1, and by ligating an Em resistance gene to the DNA fragment to be inserted into the vector. In detail, a part of the Em resistance gene was deleted by digesting pAMβ1 with AvaI and ScaI (Literature 15) to prepare a DNA fragment of about 26 kb. Separately, pBLEm211 was digested with BamHI to prepare an about 3.1 kb of a DNA fragment containing the structural gene of ST-LDH, non-translational regions of LB-LDH and an Em resistance gene. Both of the digested fragments were ligated after the end-blunting treatment. The ligation mixture was used for the transformation of 207-25 strain (Literature 17) of *Bacillus subtilis* with high transformation frequency according to the method of Chang et al. (Literature 16) Em-resistant transformants were obtained after selection on DM3 medium plates containing 25 µg/ml of erythromycin.

The obtained transformants were grown in LG culture medium (Literature 16) overnight at 37° C. with shaking and plasmid DNA was prepared according to the method of Anderson et al. (Literature 18) with some modifications. Southern hybridization was performed with DNA prepared from the transformants using Fragment L obtained in Example 3 as a probe to select transformants which hybridized. As a result of analyzing digestion patterns by restriction enzymes, the transformants contained either of two integration plasmids having restriction enzyme maps shown in FIG. 9. These integration plasmids were respectively named pβL-Int1 and pβ1-Int2. These two plasmids are collectively called pβ1-Int plasmids hereunder.

Example 5. Introduction of pβL-Int Plasmids into Lactococci

*Bacillus subtilis* strains harboring pβL-Int plasmids, namely, 207-25 (pβL-Int1) and 207-25 (pβL-Int2) were used as a donor of pβL-Int plasmids, and conjugal transfer to *Lactobacillus delbrueckii* subsp. *bulgaricus* was repeated under various conditions, but all the trials resulted in failure.

In view that conjugal transfer of pAMβ1 to *Lactobacillus delbrueckii* species was successful when *Lactococcus lactis* was used as a donor (Literature 7), the inventors tried to transfer pβL-Int plasmids into *Lactobacillus delbrueckii* species through conjugation process from *Lactococcus lactis* as a donor.

Thus, pβL-Int plasmids were introduced to *Lactococcus lactis* by conjugal transfer according to an agar plate method using the *Bacillus subtilis* strains as described above as a donor. The details are described hereunder.

*Lactococcus lactis* subsp. *lactis* M-3024 strain owned by Meiji Institute of Health Science, Meiji Milk Products Co., Ltd. (may be referred to as M-3024 strain) was cultured in a LCMG medium at 32° C. for 15 hours. The donors, *Bacillus subtilis* 207-25 (pβL-Int1) and 207-25 (pβL-Int2), were cultured with shaking at 37° C. for 15 hours in nutrient broth (Eiken Chemicals) containing 25 µg/ml of Em.

From the cultures of these donor and recipient bacteria, 1 ml portions were taken respectively and were mixed and centrifuged for 5 min. (3,000 rpm, 4° C.). The precipitated cells were washed once with a washing buffer (20 mM Tris-HCl, pH 7.0) and resuspended in 0.5 ml of the same buffer solution. A portion (0.2 ml) of the suspension was spread on an LCMG agar plate, and cultured at 32° C. for 8 hours (the conjugal transfer of pβL-Int plasmids occurs from the donor *Bacillus subtilis* to the recipient lactococcal during this culture).

After the culture, 10 ml of sterilized water was added to the agar plate to recover the cells. The cell suspension was centrifuged (3,000 rpm, 5 min, 4° C.), resuspended in 1 ml of sterilized water, diluted appropriately, and spread on the selective agar plates. The agar plates were cultured at 32° C. for 2 days under anaerobic conditions (BBL GasPak Jar; Beckton Dickinson).

Although Bacto litmus milk medium (Difco) containing 25 µg/ml of Em was used as a selective medium, it was also possible to select transconjugants on BL agar (Eiken Chemicals) plates containing 25 µg/ml of Em when culture was performed at 32° C. under anaerobic conditions.

After the obtained Em resistant colonies were purified by single colony isolation, these colonies were confirmed to be transconjugants based on the characteristics investigated. These colonies were respectively named *Lactococcus lactis* subsp. *lactis* M-3024 (pβL-Int1) and *Lactococcus lactis* subsp. *lactis* M-3024 (pβL-Int2) which may hereinafter be referred to as M-3024 (pβL-Int1) and M-3024 (pβL-Int2), respectively. These strains had the same microbiological characteristics (sugar utilization/growth temperature/cell morphology/inhibitory concentration of NaCl) as M-3024 strain had. In addition, they had a potent Em resistance (growth was possible in the presence of 1 mg/ml of Em) and, furthermore, using each strain of them as a donor, Em resistance was shown to be transferred to *Lactobacillus plantarum* JCM1149 strain by conjugal transfer experiments with a membrane filter (Literature 8). Consequently, they were found to have conjugal transfer activity.

By the above method, from *Bacillus subtilis* harboring pβL-Int1 or pβL-Int2, the relevant plasmids were able to be transferred to M-3024 strain of *lactococci*. In the following experiments, these transconjugants were used as donor in the experiments of conjugal transfer to *Lactobacillus delbrueckii* species.

Although not shown here, a conjugal transfer of pβL-Int plasmids from *Bacillus subtilis* was successfully performed using other strains of *Lactococcus lactis*. And moreover, a conjugal transfer of pβL-Int plasmids was also successful from these transconjugants of *lactococci* obtained to *Lactobacilli delbrueckii* subsp. *bulgaricus*. From these, it is apparent that other strains than M-3024 can also be successfully used as a donor.

Example 6. Integration of pβL-Int Plasmids into Chromosomal DNA of *Lactobacillus delbrueckii* subsp. *bulgaricus*

As a direct conjugal transfer from *Bacillus subtilis* was unsuccessful, M-3024 (pβL-Int1) and M-3024 (pβL-Int2) strains of *lactococci* obtained in Example 5 were used as a donor, and a conjugal transfer to *Lactobacillus delbrueckii* subsp. *bulgaricus* TS was attempted.

TS strain of *Lactobacillus delbrueckii* subsp. *bulgaricus* (may be referred to as TS strain) used as a recipient was given resistance against tetracycline, streptomycin and rifampicin by mutagenesis, and was originated from M-878 strain. However, in TS strain pBUL1 plasmid, harbored by M-878 strain, was spontaneously cured therefrom, and consequently there are no plasmids in TS strain.

TS strain was cultured at 37° C. for 15 hours in a modified LCMG medium, which had been adjusted to final pH of 5.5, containing 5 mg/ml of sodium formate (hereinafter referred to as F-LCMG culture medium). F-LCMG culture medium was used because cells of TS strain cultured in this medium showed short-rod-like shape, and the frequency of conjugal transfer was increased.

The donors, M-3024 (pβL-Int1) and M-3024 (pβL-Int2), were cultured at 32° C. for 15 hours in LCMG medium containing 25 µg/ml of Em.

The subsequent procedure for conjugal transfer was the same as Literature 7.

The donor and the recipient cells were centrifuged for 5 min. (3000 rpm), washed 3 times with a washing buffer and were suspended in the buffer solution at an optical density at 660 nm ($OD_{660}$) of 1.5, respectively. The suspensions prepared as described were mixed so that the ratio of the donor solution:recipient solution is 1:10 (v/v). A portion (300 µl) of the mixture were taken therefrom, put on a pre-sterilized membrane filter (Millipore, HAWP025; pore size=0.45 µm), sucked and filtered using a vacuum pump. Then, about 100 ml of sterilized water was passed from the upper side through the filter, and both the donor and the recipient cells were tightly held on the filter (Literature 9).

This filter was placed at the bottom of a test tube, and 3 ml of an MRS culture medium (Difco: Lactobacillus MRS Broth) containing 25% of polyethylene glycol 6000 (Fulka Chemie AG) was poured in the tube in order to soak the filter in the broth. After incubation at 37° C. for 18 hours, the test tube was applied to a vortex mixer at the maximum speed for 2 minutes so as to disperse the lactic acid bacteria caught in the filter into the medium and to obtain a homogeneous suspension. Three milliliters of MRS medium was added to the dispersion and cultured at 45° C. for 3 hours.

The whole dispersion was mixed and diluted with an MRS agar medium (Lactobacillus MRS broth: by Difco) containing Em (25 µg/ml) and 1.5% of agar which had been kept at about 50° C. before use, and was poured on 3 plates, respectively. After solidified, the plates were cultured at 45° C. under anaerobic conditions (GasPak jar).

Since the donors, *lactococcal* strains do not grow at 42° C. or more, and the recipient, *Lactobacillus delbrueckii* subsp. *bulgaricus* TS, is sensitive to Em, only the transconjugants of TS to which pβL-Int plasmid has transferred can grow under the selective conditions described above.

In 3 experiments performed at the same time, one Em resistant colony appeared after culture at 45° C. for 2 days, respectively, which was considered to have been conjugally transferred with pβL-Int1 or pβL-Int2. Single colonies from these colonies were isolated, and their characteristics were examined. As a result, they were found to be true transconjugants.

These clones were named TS::pβL-Int1 20A and TS::pβL-Int2 26A, respectively (may be referred to as 20A and 26A strains). ("TS::pβL-Int" indicates that a pβL-Int plasmid is integrated into the chromosome of TS strain).

These 20A and 26A strains showed identical microbiological characteristics to those of the recipient, TS strain, except the differences shown in Table 2. Therefore, it is apparent that these strains were derived from TS strain. Since the characteristics of 26A strain were identical to those of 20A strain, they are omitted in Table 2.

The differences from TS strain are: (1) 20A and 26A strains are resistant to Em, and (2) 20A and 26A strains produce almost the same quantities of D-lactic acid and L-lactic acid (Table 2).

It was concluded that these phenotypes were resulted from the transfer of pβL-Int plasmids. However, after the plasmids of 20A and 26A strains were prepared according to the method of Literature 18, no plasmids were detected from the transconjugants. Therefore, the pβL-Int plasmid was considered to have been integrated into the chromosomal DNA of TS strain. Actually, when Southern hybridization was performed using pAMβ1 plasmid as a probe, the probe hybridized to the chromosomal DNAs of 20A and 26A strains. From this, pβL-Int plasmids were confirmed to have been integrated into the chromosomes.

Consequently, it was clearly shown that 20A and 26A strains were transconjugants imparted with Em resistance and with ability of producing L-lactic acid by integration of pβL-Int1 or pβL-Int2 plasmid into chromosome of TS strain from M-3024 (pβL-Int1) or (pβL-Int2) strain (See FIG. 2).

TABLE 2

Characteristics of the Parent Strain (TS) and the Transconjugant (TS::pβL-Int1 20A)

| Strain | Cell morpho- logy | Growth temperature (°C.) | | | | | Utilizable sugar(*) | plasmid |
|---|---|---|---|---|---|---|---|---|
| | | 20 | 37 | 42 | 48 | 50 | | |
| TS | rod | − | + | + | + | + | Lac, Glc, Man, Fru | none |
| 20A | rod | − | + | + | + | + | Lac, Glc, Man, Fru | none |

| | Resistance to antibiotics | | | | | Optical rotation of |
|---|---|---|---|---|---|---|
| Strain | Tc-20 | Sm-200 | Rf-20 | Em-2 | Em-25 | Em-1000 | produced lactic acid (***) |
| TS | + | + | + | − | − | − | D-lactic acid 100% |
| 20A | + | + | + | + | + | + | D- and L- lactic acids |

*)Lac:lactose, Glc:glucose, Man:mannose, Fru:fructose
**)Tc:tetracycline, Sm:streptomycin, Rf:rifampicin, Em:erythromycin
Numerals indicate concentrations (µg/ml); + : resistant; − : sensitive
***)Measured by F-kit Lactic Acid (Boehringer Mannheim Yamanouchi)

Example 7. Obtaining Gene Integrants which Produce Exclusively L-Lactic Acid (1)

Figure 3:
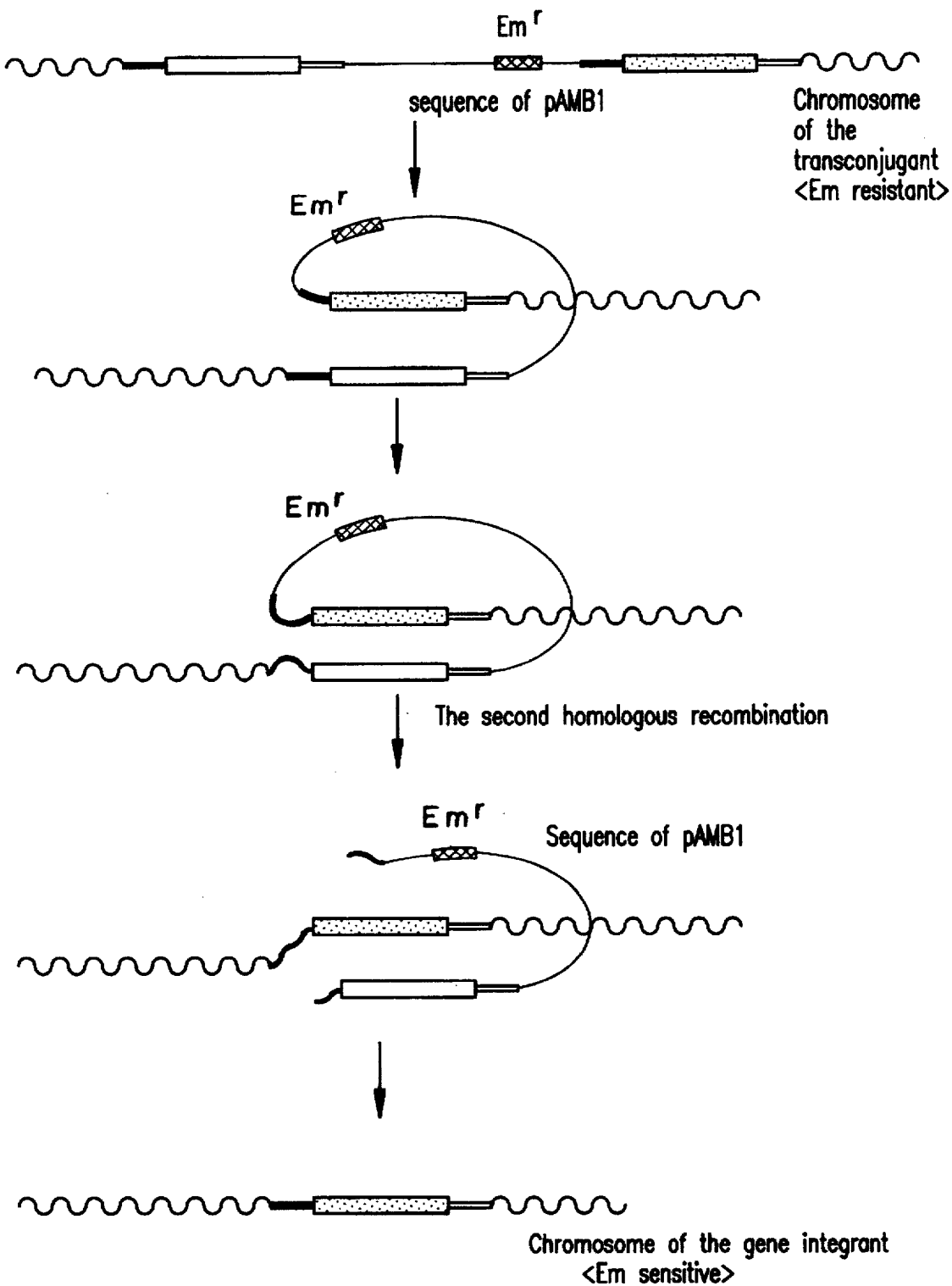
FIG. 3 is a schematic diagram of the third step of the method of gene integration into the chromosomal DNA of Lactobacillus delbrueckii species according to the present invention.

Next, subculture of the transconjugant 20A was repeated in the absence of Em, and clones were obtained which had undergone the second homologous recombination at a region in front of or behind the D-LDH gene in pβL-Int plasmid (FIG. 3).

Three single colonies on agar plates obtained from 20A were selected. They were respectively subcultured in a skim milk medium (containing 10% of skim milk and 0.1% of yeast extract: autoclaved at 121° C. for 7 min.). No radiation of ultraviolet or gamma-rays nor treatment with drugs were performed in order to avoid useless mutations or the like phenomena. Subculture was repeated 20 times by inoculating 10 µl of the solidified culture medium into 1 ml of a fresh skim milk culture medium.

Each culture medium after subculture of 20 times was appropriately diluted, spread on MRS agar plates, and anaerobically cultured in a GasPak jar at 42° C. for 1-2 days to obtain single colonies. These single colonies were picked out, inoculated on MRS agar plates with Em (25 μg/ml) or without Em. Their resistance or sensitivity to Em was judged after they were cultured under anaerobic conditions.

Three clones, obtained from 20A strain and considered identical, were subcultured as above, and 100 single colonies of each clone, 300 clones in total, were examined for sensitivity to Em. The numbers of clones sensitive to Em from each original one were 0, 3, and 11 (the rest exhibited resistance to Em).

The measurement of lactic acid produced by these 14 Em-sensitive clones revealed that 5 clones produced only L-lactic acid and 9 clones only D-lactic acid. No clones sensitive to Em produced D- and L-lactic acids simultaneously. Specifically, when 10 Em-resistant clones were randomly selected and their lactic acid production was measured, all of the 10 clones produced D- and L-lactic acids in almost the same amounts as 20A strain did.

A strain selected from these Em-sensitive clones producing only L-lactic acid was named "LL strain" (the 5 clones obtained were designated TS-LL01 through TS-LL05 strains, respectively).

These clones including TS-LL01 (deposited with Fermentation Research Institute, Agency of Industrial Science and Technology as Deposition No. FERM BP-3909) had the same characteristics as the parent TS strain with respect to cell morphology, growth temperatures, kinds of utilizable sugars, and absence of plasmids, and resistance to 3 kinds of antibiotics (tetracycline, streptomycin, and rifampicin) (see Table 2). However, resistance to Em and lactic acid production of TS-LL01 strain were different from those of the transconjugant 20A and the parent strain TS as shown in Table 3.

prepared and labelled with $^{32}p$ according to the methods of Literature 13. For pAMβ1 DNA probe, all the DNA fragments completely digested with EcoRI and HindIII were used. For LB-LDH gene DNA probe, a 0.75 kb fragment digested with HindIII and StuI was used (i.e., a DNA fragment digested at the HindIII site of the 551st of Sequence No. 1 and at StuI site at the 1275th thereof). For ST-LDH gene DNA probe, a 1.2 kb fragment of SspI was used (i.e., a DNA fragment digested at the 1701st and the 2926th SspI sites of ST-LDH (Japanese Patent Application Laid-Open (kokai) No. 251172/19919). For labeling the DNA fragments, a Multi Prime DNA Labeling System by Amersham was used.

When pAMβ1 DNA was used as a probe, hybridization was observed in the transconjugant of 20A but never in TS-LL01 strain or in the host TS strain. Therefore, it is concluded that there was no nucleotide sequences of pAMβ1 in TS-LL01 strain.

It has also become clear that TS-LL01 has ST-LDH gene but does not have LB-LDH gene, from the experiments using LB-LDH gene and ST-LDH gene DNAs as probes. From the experiments performed at the same time, it was found that TS strain has LB-LDH gene but not ST-LDH gene, and that 20A strain has both of the two genes.

From these results, it is conceivable that "gene integrants", such as TS-LL01, obtained after the subculture of the transconjugant 20A in the absence of Em were generated in the second homologous recombination as shown in FIG. 3, and pAMβ1 and D-LDH gene were lost therefrom, leaving L-LDH gene from a streptococcal strain for yogurt production. The chromosomes of TS-LL01 through LL05 are theoretically assumed to be completely the same as that of the original TS strain, except that the structural gene of D-LDH (LB-LDH) has been replaced by the structural gene of L-LDH (ST-LDH).

TABLE 3

Characteristics of TS-LL01 Strain

| Strain | Resistance to Em(*) | | | Lactic Acid Produced | Results of Hybridization (probe) | | |
|---|---|---|---|---|---|---|---|
| | Em-2 | Em-25 | Em-1000 | | pAMβ1 | LB-LDH | ST-LDH |
| TS-LL01 | − | − | − | Only L-lactic acid | − | − | + |
| 20A | + | + | + | D- and L- lactic acid | + | + | + |
| TS | − | − | − | Only D-lactic acid | − | + | − |

*) See foot note in Table 2

Thus, the strains TS-LL01 through LL05 are originated from TS strain, produce only L-lactic acid and are sensitive to Em.

Therefore, the TS-LL01 strain was considered to have been obtained as follows: after the first homologous recombination on conjugal transfer, the second homologous recombination took place at the other homologous region during subculture in the absence of Em to lose the vector of pAMβ1 and the D-LDH gene simultaneously. A strain which is sensitive to Em but produces only D-lactic acid is considered to have regained the same gene composition as that of TS strain as a result of losing pAMβ1 and L-LDH sequences simultaneously after the second homologous recombination at the same region as the fist one.

To confirm the above presumption, chromosomal DNA of each strain was isolated to carry out Southern hybridization using pAMβ1 DNA, D-LDH (LB-LDH) gene DNA, and L-LDH (ST-LDH) gene DNA as probes. These probes were Consequently, the strains of TS-LL01 through LL05 (1) produce exclusively L-lactic acid, (2) have no problem on their safety as food, (3) and are in no way inferior to the parent strain, with regard to the stability and productivity. This is a model case where the original problems have completely been solved by the invention.

Example 8. Obtaining Gene Integrants which Produce Exclusively L-Lactic Acid (2)

The results of Examples 6 and 7 were obtained using Lactobacillus delbrueckii subsp. bulgaricus TS as a recipient. In order to study the usefulness of the present invention, other strains were examined to see whether the same results would be obtained.

The type strain of Lactobacillus delbrueckii subsp. bulgaricus ATCC11842 (hereinafter may be referred to as ATCC11842 strain) was used as a recipient and pβL-Int plasmid was conjugally transferred by a similar method as applied to *Lactobacillus delbrueckii* subsp. *bulgaricus* TS in Example 6.

ATCC11842 strain was cultured at 37° C. for 15 hours in MRS medium, washed, and suspended at an optical density at 660 nm ($OD_{660}$) of 1.5. Conjugal transfer was performed as described in Example 6 using 300 μl of a solution containing the donor cell suspension of *lactococcal* M-3024 (pβL-Int2) prepared as shown in Example 6 and a cell suspension of the recipient, ATCC11842, in the ratio by volume of 1:10 (v/v).

As a result, one Em resistant colony was obtained in two series of experiments. This strain was named *Lactobacillus delbrueckii* subsp. *bulgaricus* ATCC11842::pβL-Int2 426 (hereinafter may be referred to as 426 strain). This strain was confirmed to be *Lactobacillus delbrueckii* subsp. *bulgaricus*, judging from its microbiological characteristics examined. It was also assumed that the 426 strain was a transconjugant obtained by pβL-Int2 plasmid, and the present plasmid was integrated into the chromosomal DNA of ATCC11842 strain, from the fact that the strain showed Em resistance but did not harbor plasmids, produced both D- and L-lactic acids in about the same quantities.

This 426 strain was repeatedly subcultured 25 times in the absence of Em (skim milk culture medium) as in Example 7, and single colonies were examined; Em-sensitive clones appeared about 2% of the total. The examination of the lactic acid produced by the Em-sensitive clones revealed that some clones produced only L-lactic acid, and one of them was named *Lactobacillus delbrueckii* subsp. *bulgaricus* 11842-LL201 (deposited with Fermentation Research Institute, Agency of Industrial Science and Technology as Deposition No. FERM BP-3908; hereinafter may be referred to as LL201 strain). In the Em-sensitive clones, some produced only D-lactic acid, but no strains produced both D-lactic acid and L-lactic acid simultaneously, as in Example 7.

Judging from the microbiological characteristics, LL201 strain was considered to have been derived from ATCC11842 strain. LL201 was sensitive to Em and had no plasmids, but it exclusively produced L-lactic acid. The chromosomal DNA of LL201 was examined by Southern hybridization using the entire pAMβ1 as a probe as in Example 7. As a result, hybridization experiments confirmed that the chromosome of LL201 had no pAMβ1 sequence although that of the transconjugant of 426 strain did.

Therefore, LL201 strain, like TS-LL01 strain, is considered to be a "gene integrant" in which D-LDH gene is replaced by L-LDH gene as shown in FIG. 3. Based on this, it is clear that an LL strain from the type strain of *Lactobacillus delbrueckii* subsp. *bulgaricus* was obtained by the method of the present invention. This fact indicates the usefulness of the method according to the invention more clearly.

In the above description, the results were obtained in *Lactobacillus delbrueckii* subsp. *bulgaricus*. However, this invention is not restricted thereto, and it is clear that the method of the present invention is applicable to the other two subspecies of the species *Lb. delbrueckii*, namely subsp. *lactis* and subsp. *delbrueckii*. The reason is that pAMβ1 plasmid is also integrated into chromosomal DNA of these two subspecies of Lactobacillus on conjugal transfer (Literature 7). And in addition, since the homology between DNAs of these two subspecies and *Lactobacillus delbrueckii* subsp. *bulgaricus* is extremely high (Literature 19) and the high homology to DNA nucleotide sequence of D-LDH gene is also expected, it is assumed that the pβL-Int plasmids constructed according to the present invention is also applicable to the strains of these two subspecies.

If the homology is low among the nucleotide sequences of D-LDH genes of these three species, and if the "homologous recombination" as shown in Examples 6 and 7 does not occur, D-LDH gene from an objective strain may be cloned and a favorable "integration plasmid" may be constructed like pBL-Int as shown in Examples 1 to 4.

This invention is applicable to any bacterium if only pAMβ1 plasmid is integrated into its chromosomal DNA on conjugal transfer as well as the three subspecies of *Lactobacillus delbrueckii*.

(Literatures)

1. Teuber, M. (1990), Food Biotech., 4(1), 537-.
2. Leenhouts, K. J., J. Gietema, J. Kok, and G. Venema (1991), Appl. Environ. Microbiol., 57(9), 2568-.
3. Leenhouts, K. J., J. Kok, and G. Venema (1991), J. Bcteriol., 173(5), 4794-.
4. Feirtag, J. M., J. P. Petzel, E. Pasalodos, K. A. Baldwin, and L. L. McKay (1991), Appl. Environ. Microbiol., 57(2), 539-.
5. Scheirlinck, T., J. Mahillon, H. Joos, P. Dhaese, and F. Michiels (1989), Appl. Environ. Microbiol., 55(9), 2130-.
6. Clewell, D. B., Y. Yagi, G. M. Dunny, and S. K. Schultz (1974), J. Bacteriol., 117, 283-.
7. Sasaki, Y., Y. Ito and T. Sasaki (1990), FEMS Microbiol. Rev., 87. 17 (Abstr).
8. Chassy, B. M., and E. Rokaw (1981), Molecular Biology Pathogenesis and Ecology of Bacterial Plasmids (S. Levy et al. eds.), Plenum Press, New York, p.590.
9. Sasaki, Y., N. Taketomo and T. Sasaki (1988), J. Bacteriol, 170 (12), 5935-.
10. Efthymiou, C., and C. A. Hansen (1962), J. Infect. Dis. 110, 258-.
11. Laemmli, U. K., (1970) Nature, 227, 680-.
12. Saito, H. and K. Miura, (1963) Biochim. Byophys. Acta, 72, 619-.
13. Sambrook, J. et al., (1982) Molecular Cloning; a laboratory manual, 2nd ed., Cold Spring Harbor Laboratory, Cold Spring Harbor, N.Y.
14. Bernard, N. et al., (1991) FEBS Lett., 290, 61-.
15. LeBlanc, D. J. and L. N. Lee, (1984) J. Bacteriol., 157, 445-.
16. Chang, S. and S. N. Cohen, (1979) Mol. Gen. Genet., 168, 111-.
17. Yamane, K., et al., (1984) J. Biochem. 96, 1849-.
18. Anderson, D. and L. L. Mckay, (1983) Appl. Environ. Microbiol., 46, 549-.
19. Kandler, O., and N. Weiss (1986), Bergey's Manual of Systematic Bacteriology, vol. 2 (P. H. A. Sneath, et al. eds.), Williams & Wilkins, Baltimore, p.1208-.

INDUSTRIAL APPLICABILITY

The essential feature of the present invention is to integrate an objective gene into a host chromosomal DNA using pAMβ1 as a vector, by utilizing the phenomenon that conjugally transferable plasmid pAMβ1 is not replicated in *Lactobacillus delbrueckii* species, and that the Em resistance gene is expressed only after integration into the chromosomal DNA. In addition, the point is that the position of integration on the chromosomal DNA can be assigned by inserting part(s) of the chromosomal DNA of a host bacterium in front of or behind the objective gene, and that genes unsuitable for the application to foods, such as pAMβ1 used as a vector, can be removed by repeated subculture of a transconjugant in the absence of Em.

The present invention is widely applicable to the production of foods, pharmaceuticals, feeds, etc., because an arbitrary gene is integrated into the chromosomal DNA of bacteria belonging to *Lactobacillus delbrueckii* species, and because DNA sequences of a vector pAMβ1 can be removed by the method of this invention.

According to the present invention, lactic acid bacteria of *Lactobacillus delbrueckii* species producing only D-lactic acid were improved to produce only L-lactic acid. Further, since the integrants obtained by this invention (LL strains) are assumed to have the same genetic composition as that of the original strain (recipient) except that the D-lactate dehydrogenase gene on the chromosomal DNA is substituted by an L-lactate dehydrogenase gene from a streptococcal strain used in yogurt production, the safety as food is secured, while stable L-lactic acid production is retained, and foods such as yogurt having the same characteristics as conventional ones can be produced. Production of yogurt and fermented milk products containing exclusively L-lactic acid became possible for the first time using these LL strains of *Lactobacillus delbrueckii* subsp. *bulgaricus* or *Lactobacillus delbrueckii* subsp. *lactis* as a starter lactic acid bacterium. Furthermore, L-lactic acid can be produced by conventional methods using an LL strain of *Lactobacillus delbrueckii* subsp. *delbrueckii*.

In addition, the present invention can improve or amplify other chromosomal genes of *Lactobacillus delbrueckii* species, such as protease gene and sugar utilization genes, or inactivate a specified gene. Accordingly, this invention realizes a genetic change/improvement, such as obtaining a strain deficient in restriction/modification system, which has never been reported for this bacterial species.

Moreover, the present invention enables integration of foreign genes which *Lactobacillus delbrueckii* species does not possess. For example, gene(s) to produce a sweet protein or peptide from plants can be integrated, to obtain a strain which produces a sweet constituent during fermentation of milk to dairy products; a bacteriocin production/resistance gene can be given; genes of enzymes for food production, such as amylases and proteases can be given for industrial production.

Furthermore, medical supplies, such as enzymes, hormones and vaccines, which act in digestive tracts of human beings and livestock, will be able to be produced using lactic acid bacteria of *Lactobacillus delbrueckii* species as a host.

We claim:

1. A method for integrating a gene into chromosomal DNA of a strain of *Lactobacillus delbrueckii* species, comprising the following three steps:

(1) two genomic DNA fragments on both sides of the site to be integrated on the chromosomal DNA of a *Lactobacillus delbrueckii* species are ligated upstream and downstream, respectively, of a gene to be integrated, and the resulting ligated DNA fragment is inserted into vector pAMβ1, a self transmissible plasmid, to construct an integration plasmid;

(2) introducing the plasmid constructed in step 1 into a strain of *Lactobacillus delbrueckii* species by a conjugal transfer method to obtain transconjugants exhibiting erythromycin resistance that comprise said plasmid integrated into chromosomal DNA;

(3) subculturing the obtained transconjugants under nonselective conditions in the absence of erythromycin, selecting clones which have become sensitive to erythromycin as a result of losing the DNA sequence derived from pAMβ1 plasmid by homologous recombination, and finally, from the erythromycin sensitive clones obtained, selecting gene integrants in which the gene to be integrated remains in the chromosomal DNA of the strain of *Lactobacillus delbrueckii* species.

2. The method according to claim 1, wherein the gene to be integrated includes single or multiple copies of the region coding for a protein or a peptide of the relevant gene, or includes the coding region a part of which has been deleted.

3. The method according to claim 1, wherein the gene to be integrated is an L-lactate dehydrogenase gene.

4. The method according to claim 1, wherein the two genomic DNA fragments of the chromosomal DNA to be ligated at both sides of the gene to be integrated are Fragments N and C shown in FIG. 5.

5. An integration plasmid obtained, firstly, by ligating two genomic DNA fragments at both sides of the site for integration on the chromosomal DNA of a strain of *Lactobacillus delbrueckii* species to the upstream and the downstream sites of the gene to be integrated, and secondly by binding the ligated product thus obtained with a DNA fragment coding for an erythromycin resistance gene and, finally, by inserting this bound product to an about 26 kb DNA fragment of pAMβ1 which has been obtained by digestion at the unique restriction enzyme site for AvaI on pAMβ1 plasmid and at the ScaI site on the erythromycin resistance gene of pAMβ1 with said restriction enzymes.

6. The integration plasmid according to claim 5, wherein the integration plasmid is pβL-Int1 or pβL-Int2 having a restriction map shown in FIG. 9, and having a molecular weight corresponding to about 29 kb DNA fragment.

7. A gene integrant of *Lactobacillus delbrueckii* species, wherein a gene has been added, substituted or deleted by integrating a gene into the chromosomal DNA according to the method as defined in claim 1 with the proviso that the gene which has been substituted is not identical to a native *Lactobacillus delbrueckii* gene.

8. A gene integrant of *Lactobacillus delbrueckii* species, wherein exclusively L-lactic acid is produced without producing D-lactic acid.

9. A gene integrant of *Lactobacillus delbrueckii* species, wherein the D-lactate dehydrogenase gene of the chromosomal DNA is replaced by an L-lactate dehydrogenase gene, and said gene integrant does not contain any DNA sequence derived from pAMβ1.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1949 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Lactobacillus delbrueckii ( x i ) SEQUENCE DESCRIPTION: SEQ ID NO:1:

```
GGATCCAACA  CCAGATCAAG  AGCTTGTTTG  ACCCAATGAA  CCTGCTCAAT  CCAAAGCACA     60

AGATCGATTA  AGCGGCAGCA  ATCAGCAAAT  AACATAGAAG  AAAAGTGGCA  TAACATTCTT    120

GTAAGAGAGG  ATATTATGCC  GCTTTTTGCT  TAAAAAATCC  GTTACTATAA  ACTAGCTGCA    180

GTCAAAACAT  TTTCAACTTT  GTGAAAGATA  TTTTTTTCAC  TTCAAAAATC  ATCTTGTCCA    240

TATTGATGTT  TAGCGCTTTC  ATCCAAATTA  TATTGTTCAC  GTGACTGGTT  TTTAGTGTTA    300

TCTTTCACCT  TTTTGTGTTA  CTATTATCAA  TGTAAGAGCA  AGAATAACGG  AGGGACAATT    360

ATGACTAAAA  TTTTTGCTTA  CGCAATTCGT  GAAGATGAAA  AGCCATTCTT  GAAGGAATGG    420

GAAGACGCTC  ACAAGGACGT  CGAAGTTGAA  TACACTGACA  AGCTTTTGAC  ACCAGAAACT    480

GCTGCTTTGG  CAAAGGGTGC  TGACGGTGTT  GTTGTTACC   AACAACTTGA  CTACACCGCT    540

GAAACTCTGC  AAGCTTTGGC  AGACAACGGC  ATCACTAAGA  TGAGCCTGCG  TAACGTTGGT    600

GTTGACAACA  TCGACATGGC  TAAGGCTAAG  GAACTTGGCT  TCCAAATCAC  CAACGTTCCA    660

GTTTACTCAC  CAAACGCCAT  CGCAGAACAC  GCTGCTATCC  AAGCTGCCCG  CATCCTGCGT    720
```

-continued

| | | | | | |
|---|---|---|---|---|---|
| CAAGACAAGG | CTATGGACGA | AAAGGTTGCC | CGTCACGACT | TGCGTTGGGC | ACCAACTATC | 780 |
| GGCCGTGAAG | TTCGCGACCA | AGTTGTTGGT | GTTATAGGTA | CTGGCCACAT | CGGTCAAGTC | 840 |
| TTCATGCAAA | TCATGGAAGG | CTTCGGCGCT | AAGGTTATCG | CTTACGACAT | CTTCCGCAAC | 900 |
| CCAGAATTGG | AAAAGAAGGG | CTACTACGTA | GACTCACTTG | ACGACCTGTA | CAAGCAAGCT | 960 |
| GACGTTATTT | CCCTGCACGT | TCCTGACGTT | CCAGCTAACG | TTCACATGAT | CAACGACGAG | 1020 |
| TCAATCGCTA | AAATGAAGCA | AGACGTAGTT | ATCGTTAACG | TATCACGTGG | TCCATTGGTT | 1080 |
| GACACTGACG | CGGTTATCCG | TGGTTTGGAC | TCAGGCAAGA | TCTTCGGTTA | CGCAATGGAC | 1140 |
| GTTACGAAG | GTGAAGTTGG | CATCTTCAAC | GAAGACTGGG | AAGGCAAGGA | ATTCCCAGAC | 1200 |
| GCACGTTTAG | CTGACTTGAT | CGCTCGTCCA | ACGTTCTGG | TAACTCCACA | CACTGCTTTC | 1260 |
| TACACTACTC | ACGCTGTTCG | CAACATGGTA | GTTAAGGCCT | TCGACAACAA | CCTTGAATTG | 1320 |
| GTTGAAGGCA | AGGAAGCTGA | AACTCCAGTT | AAGGTTGGCT | AATCTAGCCG | CTTAGAAATC | 1380 |
| CCTTTTTTAA | AACCTACAGA | TTTTCTTACA | ACAATCTACT | TAAAAATTAC | TTACATTACT | 1440 |
| TTACAAATAC | ATACTTTTAA | ACTTATCCAT | TAAAATCTAA | AACGAAAACC | CGCGGGGCCT | 1500 |
| TCTCACCCGC | GGGTTTTTGC | TTGCTTATTT | TTGGAGTAGA | ATATACTGAA | AGTAACTGTA | 1560 |
| AAAGAAAAAG | TGTCGCCAAT | TGCAAGAATA | AATTGAACAC | TTACCATAAC | ATCTCGTAGA | 1620 |
| TTTTGACTAT | CTACGCCGGT | AAATGCGGTC | AAGTTCGGTG | TCAAAGTACT | CTTCTGGAGT | 1680 |
| CTTGTAGTTT | AAGTCTTCCG | AGGAAGAGAG | TTGCACCATA | CCTCGATCTT | AGCAATATCT | 1740 |
| TCCACACGGT | ACTTATCCAT | ACGGTCTCCC | TTGGGAATAT | AGCGTCTGAT | AAGCCCGTTG | 1800 |
| TGCCGTTCTA | CGCTGCCTTT | ATCACAGGAT | GTATAAGGGT | GAGCGTAGTA | CACAAGAGTC | 1860 |
| TTGGAAACTT | GCTCAAGATC | GGATAGATCT | GCGAACCCAG | ATCCGTTGTC | GGTTGTGATA | 1920 |
| GACTTAAAGA | TTTGATTCCA | TTTGGATCC | | | | 1949 |

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

AACGTACACA TGATAAA                                    17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

AATGTCCATA TGATCAA                                    17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

AATGTGCATA TGATGAA                                                                                          17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

AATGTTCATA TGATTAA                                                                                          17

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:6:

GGGAATTCGG TACCAACACC AGATCAAGAG C                                                                          31

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:7:

AAATGCATAA TTGTCCCTCC GTTAT                                                                                 25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

AAATGCATAA TCTAGCCGCT TAGAA                                                                                 25

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

TGACTGCAAC TAAACTA                                                                                          17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

GTTTTTTGAA GCTTCTT                                                                                          17

( 2 ) INFORMATION FOR SEQ ID NO:11:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:11:

CAGGAAACAG CTATGAC                       17

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:12:

TAACGGAGGG ACAATTATGC ATAATCTAGC CGCTTAGAAA         40

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:13:

TAACGGAGGG ACAATTATGC A                  21

( 2 ) INFORMATION FOR SEQ ID NO:14:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:14:

TAATCTAGCC GCTTAGAAA                   19

( 2 ) INFORMATION FOR SEQ ID NO:15:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:15:

TAACGGAGGG ACAATTA                    17

( 2 ) INFORMATION FOR SEQ ID NO:16:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:16:

TAATCTAGCC GCTTAGAAA                   19

( 2 ) INFORMATION FOR SEQ ID NO:17:

( i ) SEQUENCE CHARACTERISTICS:
    ( A ) LENGTH: 11 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:17:

TGACTGCAAC T        11

( 2 ) INFORMATION FOR SEQ ID NO:18:

( i ) SEQUENCE CHARACTERISTICS:
     ( A ) LENGTH: 11 base pairs
     ( B ) TYPE: nucleic acid
     ( C ) STRANDEDNESS: double
     ( D ) TOPOLOGY: linear ( x i ) SEQUENCE DESCRIPTION: SEQ ID NO:18:

CTTCAAAAAA C        11

( 2 ) INFORMATION FOR SEQ ID NO:19:

( i ) SEQUENCE CHARACTERISTICS:
     ( A ) LENGTH: 28 base pairs
     ( B ) TYPE: nucleic acid
     ( C ) STRANDEDNESS: double
     ( D ) TOPOLOGY: linear ( x i ) SEQUENCE DESCRIPTION: SEQ ID NO:19:

TAACGGAGGG ACAATTATGA CTGCAACT        28

( 2 ) INFORMATION FOR SEQ ID NO:20:

( i ) SEQUENCE CHARACTERISTICS:
     ( A ) LENGTH: 30 base pairs
     ( B ) TYPE: nucleic acid
     ( C ) STRANDEDNESS: double
     ( D ) TOPOLOGY: linear ( x i ) SEQUENCE DESCRIPTION: SEQ ID NO:20:

CTTCAAAAAA CTAATCTAGC CGCTTAGAAA        30